United States Patent
Reinhardt et al.

(10) Patent No.: US 6,639,096 B2
(45) Date of Patent: Oct. 28, 2003

(54) PROCESS FOR THE PREPARATION OF ACYLOXYBENZENESULFONATES

(75) Inventors: Gerd Reinhardt, Kelkheim (DE); Peter Naumann, Taunusstein (DE); Miriam Ladwig, Dietzenbach (DE); Ina Golla, Rüsselsheim (DE); Torsten Pilz, Oberreifenberg (DE); Reto Wieduwilt, Kaiseraugst (CH); Henri Jourdan, Basel (CH)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/209,723

(22) Filed: Aug. 1, 2002

(65) Prior Publication Data

US 2003/0064906 A1 Apr. 3, 2003

(30) Foreign Application Priority Data

Aug. 11, 2001 (DE) .......................... 101 39 663

(51) Int. Cl.$^7$ .............................. C07C 69/00
(52) U.S. Cl. .................... 560/142; 562/56; 554/151
(58) Field of Search .................... 562/30, 45, 46, 562/47, 56; 560/129, 130, 142; 554/151, 85, 97

(56) References Cited

U.S. PATENT DOCUMENTS

| | | | | |
|---|---|---|---|---|
| 3,503,888 A | | 3/1970 | Miller et al. ............... 252/117 |
| 3,954,767 A | * | 5/1976 | Esteve-Subirana .......... 544/403 |
| 4,544,503 A | * | 10/1985 | Berry ........................ 554/90 |
| 4,587,054 A | * | 5/1986 | Hardy et al. ................ 554/90 |
| 4,666,636 A | | 5/1987 | Shen ........................ 260/512 |
| 4,705,649 A | * | 11/1987 | Balzer et al. ................ 554/90 |
| 4,721,805 A | * | 1/1988 | Nussbaum .................... 252/1 |
| 4,778,629 A | * | 10/1988 | Grabley et al. .............. 554/92 |
| 4,883,612 A | | 11/1989 | Moyne et al. .............. 260/402 |
| 5,069,828 A | | 12/1991 | Dumas et al. .............. 260/402 |
| 5,091,560 A | * | 2/1992 | Rowland ................... 554/151 |
| 5,124,475 A | * | 6/1992 | Nepras et al. ................ 554/90 |
| 5,446,840 A | * | 8/1995 | Kiuchi et al. ............... 345/545 |
| 5,523,434 A | * | 6/1996 | Burns et al. ................ 554/68 |
| 5,843,879 A | * | 12/1998 | Matsunaga et al. ......... 510/312 |
| 6,307,076 B1 | * | 10/2001 | Seebach et al. ............. 554/68 |
| 6,448,431 B1 | * | 9/2002 | Hembre .................... 560/130 |

FOREIGN PATENT DOCUMENTS

| | | |
|---|---|---|
| EP | 0 164 786 | 12/1985 |
| EP | 0 220 826 | 5/1987 |
| WO | WO 01/19771 | 3/2001 |

OTHER PUBLICATIONS

CA:125:300602 abs of JP 08217721 Aug. 27, 1996.*
CA::127:177998 abs of DE 19654780 Aug. 7, 1997.*

* cited by examiner

*Primary Examiner*—Jean F. Vollano
(74) *Attorney, Agent, or Firm*—Richard P. Silverman

(57) ABSTRACT

Process for the preparation of acyloxybenzenesulfonates by reaction of phenolsulfonate with a water content of less than 0.5% by weight and alkanecarbonyl halide in a hydrocarbon as solvent and in the presence of a catalyst in the form of a basic nitrogen-containing compound.

13 Claims, No Drawings

PROCESS FOR THE PREPARATION OF ACYLOXYBENZENESULFONATES

The invention relates to a process for the preparation of acyloxybenzenesulfonates starting from carbonyl halides and salts of phenolsulfonic acid which have a low water content.

Acyloxybenzenesulfonic acids and their salts are compounds which have been known for a long time. Depending on the chain length of the acyl group, they can be used as surfactants, bleach activators or in other applications. These compounds may be obtained by reacting sodium phenolsulfonate (SPS) with the chloride of an organic carboxylic acid. The reaction medium used is organic solvents such as methylene chloride (U.S. Pat. No. 3,503,888), high-boiling hydrocarbons (EP 220 826), xylene or toluene (EP 164 786). According to U.S. Pat. No. 5,069,828, this reaction is carried out in an aprotic organic solvent in the presence of a phase transfer catalyst.

WO 01/19 771 describes the reaction of acyl chlorides with SPS in trifluoroacetic acid (TFA) as solvent. In the examples, the ratio of TFA: SPS used is from 0.5:1 to 3:1. The high cost of TFA, its complete removal from the reaction mixture, and possible transesterification reactions or the formation of byproducts, however, prevents the utilization of the process on an industrial scale.

All of the processes have the problem that virtually anhydrous SPS must be used for the reaction since otherwise acyl halide or the finished ester are hydrolyzed in the presence of water, which leads to considerable losses in yield. SPS is available commercially as dihydrate with a water content of about 15%. Conventional drying can reduce the water content to about 2%. According to U.S. Pat. No. 5,069,828, it is possible to remove the remaining amount of water by azeotropic distillation in the presence of an entrainer such as xylene. However, due to the high time requirement, this is of little use in plants which operate continuously. Alternatively, the water content can be reduced to less than 1% by special drying in corresponding apparatuses. However, as is known from U.S. Pat. No. 4,666,636, certain drying conditions must be observed exactly since SPS can otherwise participate in a number of secondary reactions, as a result of which both the degree of conversion of the subsequent acylation, and also the color of the end products is significantly impaired. Overdrying of the SPS leads to degrees of conversion of less than 50% in the subsequent acylation reaction.

It is therefore an object of the present invention to develop a process which can be carried out industrially and also continuously, which leads, in very good yields, to the most uniform products possible which, with regard to composition, grade and color, are suitable for use in laundry detergents and cleaners. In this connection, the process should be independent of the grade of the sodium phenolsulfonate used and its pretreatment. Surprisingly, it has now been found that acyloxybenzenesulfonates can be prepared in high yields and good grades, irrespective of the grade of the SPS used, if the reaction of the SPS with an alkanecarboxylic acid derivative is carried out in an aliphatic or aromatic solvent in the presence of catalytic amounts of a nitrogen-containing organic compound having basic character.

The invention provides a process for the preparation of acyloxybenzenesulfonates by reaction of phenolsulfonates which have a water content of less than 0.5% by weight, preferably less than 0.2% by weight, of water with alkanecarboxylic acid derivatives in an aliphatic or aromatic hydrocarbon, which comprises carrying out the reaction in the presence of from 0.01 to 10% by weight of a catalyst in the form of a nitrogen-containing organic compound with basic properties.

The phenolsulfonates used as starting compounds are preferably compounds of the formula:

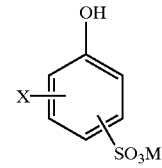

where X is hydrogen, halogen or $C_1$–$C_4$-alkyl and M is an alkali metal ion or alkaline earth metal ion.

Preference is given to sodium ortho- or para-phenolsulfonates, in particular sodium para-phenolsulfonate (SPS), which may comprise 0 to 20% of the corresponding ortho isomers as a result of the preparation.

SPS is available commercially as dihydrate, i.e. with a water content of 15%. For the inventive reaction with an alkanecarboxylic acid derivative, the phenolsulfonate must firstly be dried to a residual moisture of at most 0.5% by weight, preferably at most 0.2% by weight, of water. This can be carried out by customary methods known per se, for example in a disc drier, which permits drying to a residual moisture of less than 0.1% by weight.

The drying times may be between 1 min and 18 h depending on the equipment used, the temperatures may be between 80 and 250° C. In the process according to the invention, the quality of the dried SPS has no influence on the yield of the acylation reaction and, on average, it is possible to attain conversions greater than 95%. In particular, it is also possible to apply drying conditions which lie outside of the optimum drying conditions specified in U.S. Pat. No. 4,666,636, i.e. those which lead to "overdried" product. According to the prior art, such a product cannot be used for acylation reactions since it is not reactive enough.

The alkanecarboxylic acid derivatives which may be used are either the halides or the anhydrides. In particular, the carbonyl chlorides or bromides are suitable, preference being given to the chlorides. These can be prepared from the corresponding carboxylic acids, e.g. by reaction with phosgene, thionyl chloride, phosphorus trichloride, phosphorus oxychloride, phosphorus pentachloride or phosphorus tribromide. In the case of the anhydrides, it is possible to use symmetrical or asymmetrical compounds. Examples thereof are nonanoic anhydride, octanoic anhydride or acetylnonanoic anhydride.

The carboxylic acids which may be used are linear or branched, saturated or unsaturated alkanecarboxylic acids having 6 to 22 carbon atoms. Examples thereof are hexanoic acid, heptanoic acid, octanoic acid, methyloctanoic acid, nonanoic acid, 3,3,5-isononanoic acid, decanoic acid, undecanoic acid, undecenoic acid, lauric acid, myristic acid, hydrogenated tallow fatty acid and stearic acid. Particular preference is given to octanoic acid, nonanoic acid, isononanoic acid, decanoic acid and lauric acid. The alkanecarboxylic acid can carry further substituents, such as halogens, nitro groups or amino groups.

According to the invention, carboxylic acid derivative and phenolsulfonate can preferably be reacted together in the molar ratio from 0.9:1 to 2:1, preferably 1:1 to 1.5:1.

The reaction media used are aliphatic or aromatic hydrocarbons having boiling points between 80 and 220° C., in particular 100 to 180° C., e.g. toluene, xylene, paraffins having 8 to 22 carbon atoms, such as decane, undecane, dodecane, hexadecane or octadecane or mixtures thereof. Particularly suitable media are aliphatic hydrocarbon mixtures as are commercially available as Shellsols (Shell), ISOPAR G and ISOPAR 4 (ESSO). The solubility of the SPS in this reaction medium is often less than 1%.

The catalyst is a nitrogen-containing organic compound with basic properties. Preference is given to open-chain or cyclic tertiary amines or carboxamides. It is possible to use triethylamine, tripropylamine, dimethylformamide, diethylformamide, dimethylacetamide, tetramethylurea, substituted pyrrolidones, such as N-methylpyrrolidone, N-ethylpyrrolidone, N-butylpyrrolidone, N-octylpyrrolidone, N-methylcaprolactam, N-octylcaprolactam. Particular preference is given to triethylamine, dimethylformamide, N-methylpyrrolidone and N-octylpyrrolidone. The molar ratio of the catalyst used to the phenolsulfonate is 0.0001:1 to 0.02:1, preferably 0.005:1 to 0.012:1.

The acylation reaction is carried out at temperatures between 60 and 200° C., in particular between 100 and 150° C. The gas which forms during the reaction is withdrawn, and the reaction is optionally blanketed with a stream of inert gas comprising nitrogen or argon. The reaction is carried out as a heterogeneous reaction (slurry) since neither the phenolsulfonate nor the acyloxybenzenesulfonate which forms has a noteworthy solubility in the reaction medium. The reaction time depends on the reaction conditions and may be between 10 min and 5 h, preferably 30 to 120 min.

In a particular embodiment, the reaction according to the invention can be carried out continuously. For this purpose, reactor cascades or tubular reactors, as are known to the person skilled in the art, are particularly suitable.

When the reaction is complete, the reaction product is isolated by means of conventional separation methods. Suitable for this purpose are centrifuges, filtration apparatuses. To completely remove the catalyst, it is advisable to wash out the solid reaction product one or more times with the reaction medium. The mother liquor can be used or circulated for the subsequent reactions without further purification. The acyloxybenzenesulfonate formed is produced in high yields in the form of a white powder which can be isolated by conventional drying.

The acyloxybenzenesulfonate obtained in this way can be used as surfactant or persalt activator in laundry detergents and cleaners, such as pulverulent heavy-duty detergents, stain-removal salts or pulverulent machine dishwashing detergents. To increase the storage stability in these formulations, it can be converted into a granular form, as is known to the person skilled in the art.

EXAMPLES

Example 1a

Preparation of anhydrous 4-phenolsulfonate sodium (Good Quality)

1 kg of 4-phenolsulfonate sodium with a water content of 2.6% were dried analogously to Example 1 from U.S. Pat. No. 4,666,636. This gave 975 g of 4-phenolsulfonate sodium with a water content of <0.1%.

Example 1b

Preparation of anhydrous 4-phenolsulfonate sodium (Poor Quality)

1 kg of 4-phenolsulfonate sodium with a water content of 2.6% were dried for 12 h at 180° C. This gave 975 g of 4-phenolsulfonate sodium with a water content of <0.1%.

Comparative Example A

Use of SPS, dried in accordance with Example 1a 98.1 g (0.5 mol) of dried phenolsulfonate sodium, prepared according to Example 1, were introduced into 150 g of ISOPAR G and heated to 120° C. 114.8 g (0.65 mol) of nonanoyl chloride were added dropwise over the course of 30 min, and the mixture was after-stirred at 130° C. The HCl gas which formed during the reaction was withdrawn. The reaction mixture was cooled after 2 h to 80° C. and filtered through a filter. The white reaction product was then washed twice with a small amount of ISOPAR G and then dried overnight in a drying cabinet at 110–130° C. Tel quel yield: 164.8 g (yield 98%) of a white powder with a nonanoyloxybenzenesulfonate sodium (NOBS) content of 98%. Yield of NOBS: 96%

Comparative Example B

Use of overdried SPS, according to Example 1b 98.1 g (0.5 mol) of dried phenolsulfonate sodium, prepared according to Example 2, were introduced into 150 g of ISOPAR G and heated to 120° C. 114.8 g (0.65 mol) of nonanoyl chloride were then added dropwise over the course of 30 min, and the mixture was after-stirred at 120° C. The HCl gas which formed during the reaction was withdrawn. The reaction mixture was cooled after 2 h to 80° C. and filtered through a filter. The gray reaction product was then washed twice with a small amount of ISOPAR G and then dried overnight in a drying cabinet at 110–130° C. Tel quel yield: 129.5 g (yield 77%) of a beige-brown powder with a nonanoyloxybenzenesulfonate sodium (NOBS) content of 59%. Yield of NOBS: 45%.

Comparative Example C

Use of Overdried, Ground SPS

The procedure was analogous to that of Comparative Example B, although the SPS was ground directly prior to the start of the reaction under nitrogen using a mortar to give a very tine powder. Tel quel yield: 132.8 g (yield 79%) of a beige-brown powder with a nonanoyloxybenzenesulfonate sodium (NOBS) content of 58%. Yield of NOBS: 46%

Example 2

Addition of NOP 98.1 g (0.5 mol) of dried phenolsulfonate sodium, prepared according to Example 1b, were introduced into 150 g of ISOPAR G and heated to 120° C. 0.7 g (3.7 mmol) of N-octylpyrrolidone were added. 114.8 g (0.65 mol) of nonanoyl chloride were then added dropwise over the course of 30 min, and the mixture was after-stirred at 120° C. The HCl gas which formed during the reaction was withdrawn. The reaction mixture was cooled after 2 h to 80° C. and filtered through a filter. The white reaction product was then washed twice with a small amount of ISOPAR G and then dried overnight in a drying cabinet at 110–130° C. Tel quel yield: 165.6 g (yield 98.4%) of a white powder with a nonanoyloxybenzenesulfonate sodium (NOBS) content of 97%. Yield of NOBS: 95%. The mother liquor could be used for the subsequent batch without further purification.

Example 3

Addition of NMP 98.1 g (0.5 mol) of dried phenolsulfonate sodium, prepared according to Example 1b, were introduced into 150 g of ISOPAR G and heated to 130° C. 0.4 g (4 mmol) of N-methylpyrrolidone were added. 114.8 g (0.65 mol) of nonanoyl chloride were then added dropwise over the course of 30 min, and the mixture was after-stirred at 130° C. The HCl gas which formed during the reaction was withdrawn. The reaction mixture was cooled after 2 h to 80° C. and filtered through a filter. The white reaction product was then washed twice with a small amount of ISOPAR G and then dried overnight in a drying cabinet at 110–130° C. Tel quel yield: 164 g (yield 97.5%) of a white powder with a nonanoyloxybenzenesulfonate sodium (NOBS) content of 97%. Yield of NOBS: 95%.

Example 4

Addition of DMF 98.1 g (0.5 mol) of dried phenolsulfonate sodium, prepared according to Example 1b, were introduced into 150 g of ISOPAR G and heated to 120° C. 0.2 g (2.7 mmol) of dimethylformamide were added. 114.8 g (0.65 mol) of nonanoyl chloride were then added dropwise over the course of 30 min, and the mixture was after-stirred at 120° C. The HCl gas which formed during the reaction was withdrawn. The reaction mixture was cooled after 2 h to 80° C. and filtered through a filter. The white reaction product was then washed twice with a small amount of ISOPAR G and then dried overnight in a drying cabinet at 110–130° C. Yield: 165.7 g (yield 99%) of a white powder with a nonanoyloxybenzenesulfonate sodium (NOBS) content of 98%. Yield of NOBS: 97%.

Example 5

Addition of triethylamine 98.1 g (0.5 mol) of dried phenolsulfonate sodium, prepared according to Example 1b, were introduced into 150 g of ISOPAR G and the mixture was heated to 110° C. 0.2 g (2 mmol) of triethylamine were added. 114.8 g (0.65 mol) of nonanoyl chloride were then added dropwise over the course of 30 min and the mixture was after-stirred at 130° C. The HCl gas which formed during the reaction was withdrawn. The reaction mixture was cooled after 2 h to 80° C. and filtered through a filter. The white reaction product was then washed twice with a small amount of ISOPAR G and then dried overnight in a drying cabinet at 110–130° C. Tel quel yield: 161.14 g (yield 96.2%) of a white powder with a nonanoyloxybenzenesulfonate sodium (NOBS) content of 97%. Yield of NOBS: 93%.

Example 6

Synthesis of lauroyloxybenzenesulfonate sodium 98.1 g (0.5 mol) of dried phenolsulfonate sodium, prepared according to Example 1b, were introduced into 150 g of ISOPAR G, and the mixture was heated to 120° C. 0.7 g (3.7 mmol) of N-octylpyrrolidone were added. 142 g (0.65 mol) of lauroyl chloride were then added dropwise over the course of 30 min, and the mixture was after-stirred at 130° C. The HCl gas which formed during the reaction was withdrawn. The reaction mixture was cooled after 2 h to 80° C. and filtered through a filter. The white reaction product was then washed twice with a small amount of ISOPAR G and then dried overnight in a drying cabinet at 110–130° C. Tel quel yield: 185.4 g (yield 98%) of a white powder with a lauroyloxybenzenesulfonate sodium (LOBS) content of 98%. Yield of LOBS: 96%.

Example 7

Preparation of 2-methyloctanoyloxybenzenesulfonate sodium 98.1 g (0.5 mol) of dried phenolsulfonate sodium, prepared according to Example 1b, were introduced into 150 g of ISOPAR G, and the mixture was heated to 120° C. 0.7 g (3.7 mmol) of N-octylpyrrolidone were added. 114.7 g (0.65 mol) of 2-methyloctanoyl chloride were then added dropwise over the course of 30 min, and the mixture was after-stirred at 120° C. The HCl gas which formed during the reaction was withdrawn. The reaction mixture was cooled after 2 h to 80° C. and filtered through a filter. The white reaction product was then washed twice with a small amount of ISOPAR G and then dried overnight in a drying cabinet at 110–130° C. Tel quel yield: 160.6 g (yield 95.6%) of a white powder with a 2-methyloctanoyloxybenzenesulfonate sodium content of 95%.

What is claimed is:

1. A process for the preparation of acyloxybenzenesulfonates comprising reacting a phenolsulfonate having a water content of less than 0.5% by weight of water and an alkanecarboxylic acid derivative in an aliphatic or aromatic hydrocarbon media in the presence of from 0.01 to 10% by weight of a catalyst based on the phenolsulfonate, catalyst comprising a carboxamide compound.

2. The process as claimed in claim 1, wherein the phenolsulfonate is a compound of the formula:

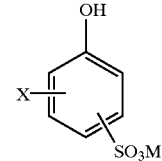

where X is hydrogen, halogen or $C_1$–$C_4$-alkyl and M is an alkali metal ion or alkaline earth metal ion.

3. The process as claimed in claim 1, wherein the phenolsulfonate is sodium phenolsulfonate.

4. The process as claimed in claim 1, wherein the alkanecarboxylic acid derivative is a $C_6$–$C_{22}$-carbonyl chloride.

5. The process as claimed in claim 1, wherein the alkanecarboxylic acid derivative and phenolsulfonate are reacted in a molar ratio of from 0.9:1 to 2:1.

6. The process as claimed in claim 1, wherein the water content of the phenolsulfonate comprises less than 0.2% by weight.

7. The process of claim 1, wherein the alkanecarboxylic acid derivative and phenolsulfonate are reacted in a molar ratio of from 1:1 to 1.5:1.

8. A process for preparing acyloxybenzenesulfonates comprising reacting a phenolsulfonate having a water content of less than 0.5% by weight of water and an alkanecarboxylic acid derivative in an aliphatic or aromatic hydrocarbon media in the presence of from 0.01 to 10% by weight of a catalyst based on the weight of phenolsulfonate, wherein the catalyst is selected from the group consisting of N-methylpyrrolidone, N-ethylpyrrolidone, N-butylpyrrolidone, N-octylpyrrolidone, N-methylcaprolactam, N-octylcaprolactam, and mixtures thereof.

9. The process of claim 1, wherein a molar ratio of catalyst to the phenolsulfonate ranges from 0.0001:1 to 0.02:1.

10. The process of claim 1 wherein the aliphatic or aromatic hydrocarbon media is selected from the group consisting of paraffins having 8 to 22 carbon atoms, aromatic hydrocarbons having boiling points between 80° C. and 220° C., and mixtures thereof.

11. A process for the preparation of acyloxybenzenesulfonates comprising:

a) reacting a phenolsulfonate having a water content of less than 0.5% by weight and an alkanecarboxylic acid derivative in a slurry media comprising an aliphatic or aromatic hydrocarbon in the presence of from 0.01 to 10% by weight based on phenolsulfonate of a catalyst selected from the group consisting of N-methylpyrrolidone and N-octylpyrrolidone, and mixtures thereof;

b) removing the acyloxybenzenesulfonates from a mother liquor comprising the catalyst and slurry media; and c) recovering the acyloxybenzenesulfonates.

12. The process of claim 11, further comprising returning the mother liquor to step (a) without further purification.

13. The process of claim 11, further comprising drying the acyloxybenzenesulfonates to a powder and granulating the powder to form a granulate.

* * * * *